(12) United States Patent
Bonrad et al.

(10) Patent No.: US 10,060,033 B2
(45) Date of Patent: Aug. 28, 2018

(54) PRECURSORS FOR THE PRODUCTION OF THIN OXIDE LAYERS AND THE USE THEREOF

(71) Applicant: MERCK PATENT GMBH, Darmstadt (DE)

(72) Inventors: Klaus Bonrad, Alsbach-Haehnlein (DE); Joerg Schneider, Seeheim-Jugenheim (DE); Rudolf Hoffman, Darmstadt (DE); Mareiki Kaloumenos, Darmstadt (DE)

(73) Assignee: MERCK PATENT GMBH, Darmstadt (DE)

( * ) Notice: Subject to any disclaimer, the term of this patent is extended or adjusted under 35 U.S.C. 154(b) by 0 days.

(21) Appl. No.: 14/915,330

(22) PCT Filed: Aug. 4, 2014

(86) PCT No.: PCT/EP2014/002140
§ 371 (c)(1),
(2) Date: Feb. 29, 2016

(87) PCT Pub. No.: WO2015/032462
PCT Pub. Date: Mar. 12, 2015

(65) Prior Publication Data
US 2016/0208386 A1 Jul. 21, 2016

(30) Foreign Application Priority Data
Sep. 3, 2013 (EP) ..................................... 13004323

(51) Int. Cl.
| | |
|---|---|
| C07F 9/66 | (2006.01) |
| C23C 18/12 | (2006.01) |
| C07F 3/00 | (2006.01) |
| C07F 5/00 | (2006.01) |
| C07F 7/00 | (2006.01) |
| C07F 7/22 | (2006.01) |
| C07F 3/06 | (2006.01) |
| H01G 4/10 | (2006.01) |
| H01G 4/33 | (2006.01) |
| H01L 21/02 | (2006.01) |
| H01L 21/445 | (2006.01) |
| H01L 29/45 | (2006.01) |
| H01L 29/66 | (2006.01) |
| H01L 29/786 | (2006.01) |

(52) U.S. Cl.
CPC .......... *C23C 18/1216* (2013.01); *C07F 3/003* (2013.01); *C07F 3/06* (2013.01); *C07F 5/003* (2013.01); *C07F 7/006* (2013.01); *C07F 7/2204* (2013.01); *C07F 7/2228* (2013.01); *C23C 18/1291* (2013.01); *H01G 4/10* (2013.01); *H01G 4/33* (2013.01); *H01L 21/02554* (2013.01); *H01L 21/02565* (2013.01); *H01L 21/02628* (2013.01); *H01L 21/02664* (2013.01); *H01L 21/445* (2013.01); *H01L 29/45* (2013.01); *H01L 29/66969* (2013.01); *H01L 29/7869* (2013.01)

(58) Field of Classification Search
CPC .. C07F 3/003; C07F 3/06; C07F 5/003; C07F 7/006
USPC ....................................... 556/35, 40
See application file for complete search history.

(56) References Cited

U.S. PATENT DOCUMENTS

| | | | |
|---|---|---|---|
| 6,174,564 B1 * | 1/2001 | Scott ................. | C23C 16/45561 427/126.3 |
| 6,310,373 B1 | 10/2001 | Azuma et al. | |
| 8,691,168 B2 | 4/2014 | Wloka et al. | |
| 9,263,591 B2 | 2/2016 | Fleischhaker et al. | |
| 2011/0233539 A1 * | 9/2011 | Seon ................... | H01L 31/1884 257/43 |
| 2012/0280228 A1 * | 11/2012 | Fleischhaker ....... | H01L 29/4908 257/43 |
| 2012/0328509 A1 * | 12/2012 | Wloka .............. | H01L 21/02422 423/622 |
| 2014/0367676 A1 * | 12/2014 | Haeming ............ | H01L 21/0237 257/43 |

FOREIGN PATENT DOCUMENTS

| | | |
|---|---|---|
| CN | 102858690 A | 1/2013 |
| GB | 1040383 | 8/1966 |
| TW | 328172 B | 3/1998 |
| TW | 201144059 A1 | 12/2011 |

OTHER PUBLICATIONS

Burrows et al., Dalton Transactions, pp. 2499-2509 (2007).*
Shapkin et al., Russian Journal of Coordination Chemistry, vol. 29, No. 8, pp. 549-553 (2003).*
Riesen et al., Journal of Physical Chemistry A, vol. 112, No. 41, pp. 10287-10293 (2008).*

(Continued)

*Primary Examiner* — Clinton Brooks
*Assistant Examiner* — Kofi Adzamli
(74) *Attorney, Agent, or Firm* — Millen White Zelano and Branigan, PC; Csaba Henter

(57) ABSTRACT

The present invention relates to novel precursors in the form of metal complexes with 2-substituted 1,3-diketones and to a process for the preparation thereof. The invention furthermore relates to the use thereof for the production of thin metal-oxide layers. The latter are constituents in a very wide variety of electronic components and devices having various functions.

11 Claims, 5 Drawing Sheets

(56) References Cited

OTHER PUBLICATIONS

Yoshida et al., Chem. Eur.J., vol. 14, pp. 10570-10578 (2008).*
Pasquarelli et al., Chem. Soc. Rev., 2011, 40, 5406-5441.*
International Search Report from PCT Application No. PCT/EP2014/002140 dated Nov. 7, 2014.
Robert M. Pasquarelli et al. "Solution Processing of Transparent Conductors: From Flask to Film" Chemical Society Reviews, (2011), vol. 40, No. 11, pp. 5406-5441.
Taiwan Search Report dated Jan. 23, 2018 issued in corresponding TW 103130288 application (1 page).

* cited by examiner

PRECURSORS FOR THE PRODUCTION OF THIN OXIDE LAYERS AND THE USE THEREOF

The present invention relates to novel precursors in the form of metal complexes with 2-substituted 1,3-diketones and to a process for the preparation thereof. The invention furthermore relates to the use thereof for the production of thin metal-oxide layers. The latter are constituents in a very wide variety of electronic components and devices having various functions.

PRIOR ART

The production of functional ceramic layers by application of solutions or dispersions offers many technical advantages as a shaping process. Depending on the substrate to be coated and the oxidic layers to be deposited, a very wide variety of processes and a multiplicity of techniques have been developed which allow both the production of two-dimensional and also structured coatings. The application of chemical compositions which serve as starting materials for the formation of the layers can be carried out, for example, by spin coating, spray coating or ink-jet printing. Compared with high-vacuum techniques, these application methods are generally less complex in terms of equipment and are advantageously more suitable for continuous production lines, facilitating performance on an industrial scale more easily.

Basically two different routes are available for the preparation of suitable coating solutions or dispersions.

On the one hand, suitable particles for the formation of the oxide layers to be applied can be converted into a dispersion with addition of additives, such as, for example, liquefiers, stabilisers, binders or antifoams. After application and drying of the dispersion on the substrate, burning out of the organic additives is necessary. Alternatively, it is possible to employ solutions of suitable chemical compounds which serve as precursors for the oxidic coating to be produced.

Such solutions typically have a longer shelf life and greater stability than dispersions of particles. After application to the substrate, conversion into the desired oxide by heat treatment is necessary here.

A common feature of the two processes is that the temperatures necessary for performance extend over a range of several hundred degrees. For the production of complex components, however, treatment at very high temperatures is usually undesired, since this restricts the choice of substrates to be coated and interfering reactions at interfaces and interdiffusion may occur. Various ways of reducing the process temperature have been adopted in the past. Besides optimisation of the process parameters, chemical modification on the molecular skeleton of the ligands in the metal complex is possible in the case of the use of precursors.

However, the production of functional oxidic layers from precursors by application from a solution and subsequent thermal processing is still restricted in its range of applications. For deposition from a solution, good solubility of the precursors in solvents which are suitable for the coating, stability of the solution under ambient and coating conditions, wetting of the substrate by the solution and the lowest possible conversion temperature in a narrow temperature range are necessary. The use of precursors, which are usually employed in vacuum processes, such as, for example, in the CVD (chemical vapour deposition) process, is thus generally not possible, since thermally stable and readily sublimable compounds are used for this process. For deposition from solution, by contrast, even slight sublimation during conversion into the oxidic layer, in particular in the case of multinary or multi-phase systems, is undesired, since the formation of a defined composition is made more difficult.

A group of precursors that has been used to date is a ligand system in the form of condensation products of so-called Schiff's bases ("oximates"), in particular methoxyiminopropionic acid. The use of these compounds offers many advantages with respect to processing, film formation and aftertreatment in the deposited film. Thus, a semiconducting layer, which can be used in thin-film transistors, can be produced, for example, after thermal conversion. Disadvantages in the use of this class of compounds, besides the still-high decomposition temperatures, are difficulties in preparing same without trace contamination by alkali metal or halide ions. Furthermore, the starting materials for the condensation reaction of the Schiff's base, i.e. alpha-keto acids and O-alkoxylamines, can only be modified to a limited extent without major effort, since a large number of synthesis steps is necessary, which, however, result in low yields.

OBJECT TO BE ACHIEVED

The object of the present invention is therefore to provide a process for the preparation of suitable precursors which can be carried out simply and reliably, which avoids the disadvantages described and which can be carried out by means of an easily derivatised ligand system, where the precursors prepared in this way can be converted into the corresponding metal oxide in a simple manner at the lowest possible temperatures without the formation of significant proportions of organic residues which have to be expelled by heat treatment. The object of the present invention is thus also to provide ligands which readily decompose to give volatile constituents.

SUBJECT-MATTER OF THE INVENTION

It has now been found that the object according to the invention can be achieved by novel metal complexes with 2-substituted 1,3-diketones of the general formula (I)

$$M_l[R^1-CO-C(H)_m X-CO-R^2]_n, \qquad (I)$$

in which
M denotes a metal atom selected from the group zinc, indium, gallium, tin, aluminium, zirconium, titanium and hafnium,
l denotes 1 or 2, in the case of cluster formation ≥2,
m denotes 0 or 1,
n denotes 1, 2, 3 or 4, in the case of cluster formation >2,
$R^1$, $R^2$, independently of one another, denote alkyl having 1 to 8 C atoms,
  cycloalkyl having 3 to 7 C atoms,
  alkoxy having 1 to 8 C atoms
  or amino, $NHR^3$, $NR^3R^4$, where $R^3$, $R^4$, independently of one another, denote alkyl having 1 to 8 C atoms or cycloalkyl having 3 to 7 C atoms,
  and
X denotes H, hydroxyimino, nitro, sulfo, including —$SO_2$-alkyl having 1 to 8 C atoms, phosphato, including —PO(O—R)$_2$, where R=alkyl having 1 to 8 C atoms or alkoxy having 1 to 8 C atoms;
  stannyl —$SnR_3$, where R=alkyl having 1 to 8 C atoms;
  mercapto —SR, where R=H, alkyl having 1 to 8 C atoms or cycloalkyl having 3 to 7 C atoms, halide, such as F, Cl, Br or I, or pseudohalide, such as —CN, —N$_3$, —OCN, —NCO, —CNO, —SCN or —SeCN, in particular by 1,3-diketones in which R$^1$, R$^2$, R$^3$ and R$^4$, independently of one another, denote methyl, ethyl, propyl, butyl, pentyl, cyclopropyl, cyclo-butyl, cyclopentyl, cyclohexyl, methoxy, ethoxy, propoxy and in the case of R$^1$ and R$^2$ denote amino. X or HX in these 1,3-diketones preferably adopts the meaning hydroxyimino, nitro, sulfo, including —SO$_2$-alkyl having 1 to 8 C atoms, halide, such as F, Cl, Br or I, or pseudohalide, such as —CN, —N$_3$, —OCN, —NCO, —CNO, —SCN or —SeCN. From this group of 1,3-diketones, compounds selected from the group nitrodimethyl malonate, hydroxyimino-dimethyl malonate and nitromalonic acid diamide are particularly suitable for achieving the object according to the invention. These 1,3-diketones as ligands, with a metal atom M selected from the group zinc, indium, gallium, tin, aluminium, zirconium, titanium and hafnium, form metal complexes of the general formula (I), which can be converted into the corresponding metal oxides, even at low temperatures. If desired, corresponding complexes of other metals not listed here can also be prepared in the same way. Owing to the properties of the ligands presented here, these metal complexes have low decomposition temperatures in the same way and can be employed in the same way as the complexes described here. Experiments have shown that metal complexes of the 1,3-diketone(s) of the general formula (I) selected from the group nitrodimethyl malonate, hydroxyiminodimethyl malonate and nitromalonic acid diamide are particularly suitable for the desired conversion into the corresponding metal oxides with formation of a thin, optionally ceramic, oxide layer and decomposition of the ligands to give volatile constituents.

The metal complexes of the general formula (I) according to the invention can be in the form of clusters, which form through association of metal-complex molecules and optionally with liberation of individual ligands. Correspondingly, the number l in such clusters adopts a value greater than or equal to 2. The number n increases correspondingly and is greater than 2.

In order to carry out the process for the production of thin metal-oxide layers, one or more metal complex(es) as described above is (are) dissolved or dispersed in a suitable solvent or solvent mixture, optionally in the presence of water,
the solution or dispersion obtained, to which further additives selected from the group liquefiers, stabilisers, binders and antifoams and optionally others have optionally been added, is applied by means of wet coating to a substrate surface to be coated, dried,
and in a further step the metal-complex layer applied is converted into a metal oxide in the form of a thin layer by means of heating in an oven, on a hotplate or by means of irradiation by UV, IR or laser.

For the preparation of the solution or dispersion, solvents selected from the group methoxyethanol, dimethylformamide and dimethoxyethane, which can be employed in pure form or in a mixture, optionally also in the presence of water, are particularly suitable.

The solution or dispersion comprising the metal complex can be applied to the substrate surface in this process by means of spin coating, dip coating, spray coating, gravure printing, ink-jet printing or flexographic printing. The process is particularly advantageous if the solution or dispersion comprising the corresponding metal complex comprises solvents selected from the group methoxyethanol, dimethylformamide and dimethoxyethane, individually or in a mixture, and optionally water. The conversion of the metal-complex layer applied in this way and dried into a thin oxide layer can surprisingly be carried out by heating and calcination at lower temperatures than in comparable known processes, preferably at temperatures in the range from 150-350° C. In this way, thin ceramic oxide layers of the metals zinc, indium, gallium, tin, aluminium, zirconium, titanium and hafnium or other suitable metals can be produced in accordance with the invention in a process which is simple to carry out. In particular, layers in which the oxides are present in pure form or in a mixture, or as mixed oxides, can be produced in this way.

If necessary for the formation of sufficiently thick or of dense homogeneous layers, the solution or dispersion is applied a number of times to the substrate surface before the heating and calcination, with each layer being dried and heated individually.

The process provided hereby is universally applicable, and the novel metal complexes which contain ligands in the form of the 1,3-diketones of the general formula (I) can be used for the production of thin metal-oxide layers in electronic components, such as capacitors or thin-film transistors, in photovoltaics, semiconductor technology or as anti-scratch or antireflection layers. However, the process is also suitable for the production of thin metal-oxide layers in solar cells, flat-panel screens and touch screens, or as semiconductors in field-effect transistors using these metal complexes according to the invention.

DETAILED DESCRIPTION OF THE INVENTION

Experiments have surprisingly shown that a novel class of materials of metal complexes with 2-functionalised 1,3-diketones of the general formula (I)

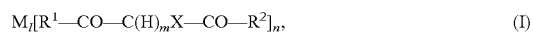

$$M_l[R^1\text{—CO—C(H)}_m X\text{—CO—}R^2]_n, \quad (I)$$

where
M denotes a metal atom selected from the group zinc, indium, gallium, tin, aluminium, zirconium, titanium and hafnium,
l denotes 1 or 2, in the case of cluster formation ≥2,
m denotes 0 or 1,
n denotes 1, 2, 3 or 4, in the case of cluster formation >2,
R$^1$ and R$^2$, independently of one another, denote alkyl having 1 to 8 C atoms,
cycloalkyl having 3 to 7 C atoms,
alkoxy having 1 to 8 C atoms and/or amino, NHR$^3$ or NR$^3$R$^4$,
where R$^3$ and R$^4$, independently of one another, denote alkyl having 1 to 8 C atoms or cycloalkyl having 3 to 7 C atoms,
and
X denotes H, hydroxyimino, nitro, sulfo, including —SO$_2$-alkyl having 1 to 8 C atoms, phosphato, including —PO(O—R)$_2$, where R=alkyl having 1 to 8 C atoms or alkoxy having 1 to 8 C atoms;
stannyl —SnR$_3$, where R=alkyl having 1 to 8 C atoms;
mercapto —SR, where R=H, alkyl having 1 to 8 C atoms or cycloalkyl having 3 to 7 C atoms, halide, such as F, Cl, Br or I, or pseudohalide, such as —CN, —N$_3$, —OCN, —NCO, —CNO, —SCN or —SeCN,
is particularly suitable for the requirements described. This likewise applies to clusters of these metal complexes of the general formula (I) which arise through association and optionally liberation of ligands, resulting in l and n each, independently of one another, adopting a value greater than or equal to 2. In such clusters, l can adopt a value of several thousand. The same also applies correspondingly to n. l in a cluster of the metal complexes of the general formula (I) usually denotes a number ≥2 to 160. The number for n changes depending on the number of associated metal-complex molecules. For the purposes addressed here, clusters in which the number of metal nuclei l is in the range ≥2 to 40 are suitable.

For the synthesis of the metal complexes, a selection can be made from a multiplicity of ligands, since the functionalisation of 1,3-diketones [$R^1$—CO—CH$_2$—CO—$R^2$, where $R^1$, $R^2$=as listed above alkyl, alkoxy and/or amino (NH$_2$, NHR$^3$ or NR$^3$R$^4$)] in the 2-position is possible by a very wide variety of groups X or HX in a simple manner, both for corresponding diketones in which the bonding of the groups in the 2-position takes place by single or by double bond. Few steps are necessary for the synthesis, which simultaneously result in good yields. The groups X and HX can be, as listed above, hydroxyimino (=NOH), nitro (—NO$_2$), sulfo (—SO$_2$(R)), phosphato (—PO(OCH$_3$)$_2$), alkoxy (—OR), stannyl (—SnR$_3$), mercapto (—SH or —SR), halide, such as F, Cl, Br or I, or pseudohalide, such as —CN, —N$_3$, —OCN, —NCO, —CNO, —SCN or —SeCN, where the radicals R can have the meanings given above.

These ligands can typically be purified well by distillation, sublimation or re-crystallisation.

Owing to the acidity of the ligands, the subsequent synthesis of the metal complexes can be carried out using compounds of the metals themselves which form the desired complex with the selected ligand system, such as, for example, alkoxides, alkyls, carboxylates or carbonates of the metals. This enables contamination by alkali metals or halides to be considerably reduced or completely prevented. However, the use of other metal compounds, such as halides, nitrates or other salts, is in principle likewise possible. Suitable metal compounds for the preparation of the complex system are, in particular, alkoxides, alkyls, carboxylates, halides or carbonates of the metals zinc, indium, gallium, tin, aluminium, zirconium, titanium and hafnium. Restrictions regarding the metal element present in the complex only exist with respect to unusual oxidation states which still have strongly oxidising or reducing properties, even in the complex. The latter are unsuitable for the purposes of the present invention.

In accordance with the invention, the decomposition process of the metal complex prepared to give the corresponding metal oxide, and thus also the decomposition temperature, can be significantly influenced by the choice of functionalisation by X or XH, but also by the substituents $R^1$ and $R^2$. In addition, improved solubility is achieved in accordance with the invention by a simple modification of the substituents of the ligand of the metal complex of the general formula (I). This is possible, in particular, through the choice of $R^1$ and $R^2$, but in particular also through the introduction of suitable groups X or HX. An increase in the solubility of the metal complexes can be achieved through a suitable choice of the substituents. At the same time, it is possible to increase the range of solvents that can be employed through the substituents selected.

Experiments carried out have shown that the metal complexes described here of the 2-functionalised 1,3-diketones of the general formula (I)

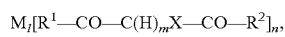

can be converted into an oxide layer at surprisingly lower temperatures.

As has been shown, the novel, readily accessible precursors are generally suitable for the deposition of thin oxidic layers from solution. Broad application of this class of compounds in very different sectors is thus possible.

Besides the use for the production of electronic switching elements (thin-film transistors), their use in processes in photovoltaics or for the production of antiscratch or antireflection layers is also possible.

The oxide layers produced in this way at low temperatures meet, in particular, the high requirements made of functional layers, for example in the production of semiconductors in field-effect transistors.

Accordingly, the present invention
a) provides a synthesis route for novel metal complexes which can be converted into the corresponding metal oxides in the form of thin layers at lower temperatures with liberation of readily volatile organic decomposition products
and
b) provides novel precursors in the form of metal complexes which can be employed in a process step which can be carried out simply and reliably in the production of field-effect transistors and other electronic components,
c) enabling these novel materials and metal complexes to be employed in industrial areas, such as, for example, in optical applications for the production of antireflection layers, etc., or as mechanical protection layers in the form of antiscratch layers.

The ligands according to the invention and the metal complexes serving as precursors for the production of the thin metal-oxide layers can be prepared by methods which are generally known from the literature and to the person skilled in the art.

Accordingly, the ligands and metal complexes used in the following examples can be synthesised by known literature processes. The starting material employed can be commercially available 1,3-diketones [$R^1$—CO—CH$_2$—CO—$R^2$, where $R^1$, $R^2$=alkyl, alkoxy and/or amino (NH$_2$, NHR$^3$ or NR$^3$R$^4$)]. The functionalisation in the 2-position is likewise carried out by processes known from the literature.

The nitrosation of the 1,3-diketones where the radicals $R^1$ and $R^2$ have the meaning alkyl or alkoxy can be carried out in accordance with the examples described by H. Adkins and E. W. Reeve (*J. Am. Chem. Soc.* 1938, 60, 1328-1331). Nitrosation of the 1,3-diketones where $R^1$ and $R^2$ have the meaning amino can be carried out by the method of M. A. Whiteley (*J. Chem. Soc. Trans.* 1900, 77, 1040-1046) or as described by M. Conrad and A. Schulze in *Ber. Deut. Chem. Gesell.* 1909, 42, 729-735. Nitration of the 1,3-diketones where $R^1$ and $R^2$ have the meaning alkoxy can be carried out by methods as described in the following reference: D. I. Weisblat, D. A. Lyttle, U.S. Pat. No. 2,644,838. The nitration of the 1,3-diketones where the radicals $R^1$ and $R^2$ have the meaning alkyl or alkoxy can also be carried out by the method of A. L. Laikhter, V. P. Kisiyi, V. V. Semenov (*Mendeleev Commun.* 1993, 3, 20-21) or by the method of S. Sifniades (*J. Org. Chem.* 1975, 40, 3562-3566). The nitration of the 1,3-diketones where the radicals $R^1$ and $R^2$ have the meaning amino can in turn be carried out by the method of M. Sebban, J. Guillard, P. Palmas and D. Poullain (*Magn. Reson. Chem.* 2005, 43, 563-566). Sulfonation of the 1,3-diketones where the radicals $R^1$ and $R^2$ have the meaning alkyl or alkoxy can be carried out by the method of H. Böhme and R. Marx (*Ber. Deut. Chem. Gesell.* 1941, 74, 1664-1667).

The ligands described in the examples, which have been used by way of example for the production of metal-oxide layers according to the invention, can also be prepared by these methods known from the literature.

Derivatised 1,3-diketones of the formula (I) can be reacted, as described above, in a simple manner with the above-mentioned metal compounds to give the desired metal complexes, which can be employed as precursors for the production of thin metal-oxide layers. Depending on the radicals $R^1$, $R^2$ and the substituents X and HX, the metal complexes can be converted into the metal oxides by heating to temperatures up to 600° C., for example by irradiation by UV, IR or laser, where the organic decomposition products liberated evaporate. Preference is given in this connection to metal complexes which are soluble as far as possible in aqueous systems and are converted into the corresponding metal oxides on heating at lower temperatures, in particular at temperatures in the range from 150 to 350° C. Experiments have shown that metal complexes of the ligands 2-nitrodimethyl malonate and 2-hydroxyiminodimethyl malonate are particularly suitable, both with respect to the solubility and also the conversion temperature.

For the production of metal-oxide layers, the metal complexes according to the invention as precursors or intermediates are firstly dissolved in a solvent having suitable volatility and viscosity, such as, for example, in methoxyethanol, dimethylformamide or dimethoxyethane, optionally in the presence of water. The application to the substrate surface can be carried out by wet coating by known methods, such as spin coating, dip coating, spray coating, ink-jet printing, flexographic printing or gravure printing. Suitable coating methods from solutions are described by R. M. Pasquarelli et al. in *Chem. Soc. Rev.*, 2011, 40, 5406-5441. The conversion of the applied metal complexes into the desired oxidic coating is carried out after drying in a further step by means of heating in an oven or on a hotplate or by means of irradiation by UV, IR or laser, where, in accordance with the invention, the oxidic material forms in the form of a thin layer. In order, in particular cases, to produce sufficiently thick layers, the steps of application of solution, drying and heating can be repeated a number of times. It is also possible here to carry out the various application steps with solutions of different metal complexes, so that layers comprising different metal oxides form. However, it is also possible to dissolve two or more different metal complexes in the solution to be applied, so that, after conversion by heating, or calcination, mixed oxides of different metals are obtained.

The present description enables the person skilled in the art to apply and carry out the invention comprehensively. Even without further comments, it will therefore be assumed that a person skilled in the art will be able to utilise the above description in the broadest scope.

If anything is unclear, it goes without saying that the cited publications and the patent literature should be consulted. Accordingly, these documents are regarded as part of the disclosure content of the present description.

For better understanding and in order to illustrate the invention, examples are given below which lie within the scope of protection of the present invention. These examples also serve to illustrate possible variants. Owing to the general validity of the inventive principle described, however, the examples are not suitable for reducing the scope of protection of the present application to these alone.

Furthermore, it goes without saying to the person skilled in the art that, both in the examples given and also in the remainder of the description, the component amounts present in the compositions always only add up to 100% by weight or 100 mol-%, based on the entire composition, and cannot exceed this, even if higher values could arise from the per cent ranges indicated. Unless indicated otherwise, % data are regarded as % by weight or mol-%, with the exception of ratios, which are reproduced in volume data, and for the preparation where solvents, for example, are used in certain volume ratios in the mixture.

The temperatures given in the examples and description and in the claims are always in ° C.

EXAMPLES

The working examples reproduced below correspond to the so-called "best mode" examples, as exist at the time of filing of the application.

Example 1

Synthesis of the zinc complex with nitrodimethyl malonate 10 g (56.8 mmol) of 2-nitro-1,3-dimethyl malonate are initially introduced in 200 ml of dist. water. After addition of 10 g (91.1 mmol of Zn) of hydrozincite, a yellow suspension forms, which is stirred for a further 3 hours. The excess of hydrozincite is then filtered off, and the solution is evaporated to dryness in a rotary evaporator at 65° C. and 130 mbar. The yellow oil remaining is taken up in 50 ml of dichloromethane and filtered. The product is precipitated by dropwise addition of the solution to 200 ml of methyl tert-butyl ether, filtered off and dried in a high vacuum at room temperature, giving a pale-yellowish powder (6.4 g, 34.2%).

Ceramic yield (CY)/elemental analysis (CHN): found CY 39.87%, C, 19.86%, N, 4.50%, H, 2.78%. Calculated for $Zn_3(OH)_4(C_5H_6NO_6)_2$ CY 39.63%, C, 19.49%, N, 4.54%, H, 2.62%. $^1$H-NMR (DMSO-$d_6$): 3.57 (—$CH_3$), 3.40 (OH). $^{13}$C-NMR/$^{13}$C-DEPT-NMR (DMSO-$d_6$): 50.91 (—$CH_3$); 109.07 (—C—$NO_2$); 163.72 (—COO). IR: 3460 cm$^{-1}$, v br (vO—H).

Example 2

Synthesis of the zinc complex with hydroxyiminodimethyl malonate

Under protective gas, solutions of zinc 2-propanolate (1.33 g, 7.2 mmol) and 2-hydroxyiminodimethyl malonate (3.50 g, 21.7 mmol) are prepared in 10 ml of tetrahydrofuran in each case. The solution of the zinc compound is subsequently cooled to 0° C., and the ligand is added dropwise. The solution immediately becomes a yellow colour, and a precipitate forms on warming to room temperature. The product is filtered off, washed twice with 10 ml of methyl tert-butyl ether each time and dried in a high vacuum at room temperature for several hours, giving 1.84 g (82.3%) of a yellowish powder. The product is stable under ambient conditions.

Ceramic yield (CY)/elemental analysis (CHN): found CY 26.50%, C, 29.52%, N, 6.60%, H, 2.98%. Calculated for $Zn_4O(C_5H_8NO_5)_2$ CY 26.29%, C, 29.10%, N, 6.79%, H, 2.92%. $^1$H-NMR (DMSO-$d_6$): 3.69, 3.72 (—$CH_3$). $^{13}$C-NMR/$^{13}$C-DEPT-NMR (DMSO-$d_6$): 51.62 (—$CH_3$); 143.36 (—C=NO); 162.70, 164.69 (—COO).

Example 3

Synthesis of the zinc complex with nitromalonic acid diamide 15 ml of a 1.0 M aqueous solution of tetramethylammonium hydroxide are added to nitromalonamide (2.19 g, 15.00 mmol). The yellow solution formed is stirred for 30 minutes. Solid zinc nitrate hexahydrate (2.23 g, 7.50 mmol) is subsequently added. A white solid precipitates out, which is filtered off and washed twice with 10 ml of cold water each time. Drying gives 2.38 g (80.67%).

Ceramic yield (CY)/elemental analysis (CHN): found CY 21.53%, C, 18.75%, N, 21.18%, H, 3.15%. Calculated for $Zn(C_3H_4N_3O_4)_2(H_2O)_2$ CY 20.68%, C, 18.31%, N, 21.35%, H, 3.07%. $^1$H-NMR (DMSO-$d_6$): 9.23, 7.78 (br, —$NH_2$), 3.39 (br, $H_2O$). $^{13}$C-NMR/$^{13}$C-DEPT-NMR (DMSO-$d_6$): 112.46 (—C—$NO_2$); 168.36 (—$CONH_2$).

Example 4

Synthesis of the tin(II) complex with nitrodimethyl malonate

Under protective gas, a solution of 1.96 g (11.07 mmol) of 2-nitrodimethyl malonate in 10 ml of methyl tert-butyl ether is added to 1.0 g (5.53 mmol) of tin(II) methoxide. The suspension is subsequently stirred for one hour, the solid is filtered off and washed twice with 10 ml of methyl tert-butyl ether. Drying in a high vacuum gives the product in the form of a yellow powder (2.06 g). The product is stable under ambient conditions.

Ceramic yield (CY)/elemental analysis (CHN): found CY 64.25%, C, 13.85%, N, 2.93%, H, 2.12%. Calculated for $Sn_4(OH)_6(C_5H_6NO_6)_2$ CY 64.58%, C, 12.93%, N, 3.02%, H, 1.95%. $^1$H-NMR (DMSO-$d_6$): 3.83 (—$CH_3$), 3.50 (OH). $^{13}$C—NMR/$^{13}$C-DEPT-NMR (DMSO-$d_6$): 52.09 (—$CH_3$); 143.24 (—C—$NO_2$); 160.33 (—COO). IR: 3446 $dm^{-1}$, v br (vO—H).

Example 5

Synthesis of the indium complex with nitrodimethyl malonate

Under protective gas, 1.5 g (4.49 mmol) of indium butoxide are dissolved in 10 ml of toluene, and a solution of 2.39 g (13.49 mmol) of 2-nitrodimethyl malonate in 10 ml of toluene is added. A yellowish-white solid immediately precipitates out. The product is filtered off, washed twice with 10 ml of toluene each time and dried in a high vacuum, giving a yellowish-white powder (1.93 g), which is stable under ambient conditions.

Ceramic yield (CY)/elemental analysis (CHN): found CY 41.83%, C, 26.77%, N, 4.18%, H, 3.22%. Calculated for $In_3O_3(C_5H_6NO_6)_3(C_7H_8)$ CY 41.11%, C, 26.09%, N, 4.15%, H, 2.59%. $^1$H-NMR (DMSO-$d_6$): 3.73 (—$CH_3$). $^{13}$C-NMR/$^{13}$C-DEPT-NMR (DMSO-$d_6$): 50.03 (—$CH_3$); 108.14 (—C—$NO_2$); 162.67 (—COO).

Example 6

Synthesis of the zirconium complex with hydroxyiminodimethyl malonate

Under protective gas, 1.0 g (3.1 mmol) of zirconium 1-propanolate (70% by weight in 1-propanol) is dissolved in 2 ml of tetrahydrofuran. The solution of 2.0 g (12.4 mmol) of 2-hydroxyiminodimethyl malonate in 4 ml of tetrahydrofuran is added. The reaction mixture is stirred for a further 30 minutes. The solvent is distilled off to dryness in vacuo, and the oil remaining is taken up in 3 ml of methyl tert-butyl ether/chloroform (v:v; 1:1). The product is precipitated by dropwise addition to 60 ml of pentane, filtered off and dried in a high vacuum, giving a yellowish-white powder (yield: 1.21 g, 56.3%), which is stable under ambient conditions.

Ceramic yield (CY)/elemental analysis (CHN): found CY 29.21%, C, 29.17%, N, 6.32%, H, 3.48%. Calculated for $Zr_6O_4(OH)_4(C_5H_8N)_{12}$ CY 28.43%, C, 27.71%, N, 6.46%, H, 2.95%. $^1$H-NMR (DMSO-$d_6$): 3.78, 3.84 (—$CH_3$), 3.57 (OH). $^{13}$C-NMR/$^{13}$C-DEPT-NMR (DMSO-$d_6$): 50.53 (—$CH_3$); 142.18 (—C—$NO_2$); 163.10, 160.56 (—COO). IR: 3430 $cm^{-1}$, v br (vO—H).

Example 7

Synthesis of the zirconium complex with nitrodimethyl malonate

Under protective gas, 1.0 g (3.1 mmol) of zirconium 1-propanolate (70% by weight in 1-propanol) is dissolved in 2 ml of toluene. A solution of 2.0 g (12.4 mmol) of 2-nitrodimethyl malonate in 4 ml of toluene is added. The reaction mixture is stirred for a further 30 minutes. The solvent is condensed off to dryness in vacuo, and the oil remaining is taken up in 3 ml of methyl tert-butyl ether/chloroform (v:v; 1:1). The product is precipitated by dropwise addition to 60 ml of pentane, filtered off and dried in a high vacuum, giving a yellowish-white powder (yield: 1.21 g, 56.3%), which is stable under ambient conditions.

Ceramic yield (CY)/elemental analysis (CHN): found CY 27.17%, C, 27.52%, N, 5.83%, H, 2.84%. Calculated for $Zr_6O_4(OH)_4(C_5H_8NO_6)_{12}$ CY 26.47%, C, 25.81%, N, 6.02%, H, 2.74%. $^1$H-NMR (DMSO-$d_6$): 3.80 (—$CH_3$), 3.67 (OH). $^{13}$C-NMR/$^{13}$C-DEPT-NMR (DMSO-$d_6$): 48.54 (—$CH_3$); 108.43 (—C—$NO_2$); 163.10 (—COO). IR: 3436 $cm^{-1}$, v br (vO—H).

The metal complexes prepared in accordance with Examples 1-6 can now be taken up, as described above, in a suitable solvent and applied to the substrate by wet coating, as described by R. M. Pasquarelli et al. in *Chem. Soc. Rev.*, 2011, 40, 5406-5441, and converted into the desired ceramic coating after drying.

Example 8

Production of Thin-film Transistors

Substrates for field-effect transistors consist of highly n-doped silicon with a dielectric layer of silicon dioxide (90 nm), to which gold electrodes (40 nm) with an interlayer of indium tin oxide (5 nm) are applied. The electrodes are arranged in the form of an interdigital structure with a channel width W of 10 mm and a channel length L of 10 μm (detailed description and figures in J. J. Schneider et al., Adv. Mater. 2008, 20, 3383-3387). The charge-carrier mobility $\mu_{SAT}$ and the threshold voltage $V_{th}$ are determined by linear adaptation of the square root of the source/drain current ($I_{DS}^{0.5}$) as a function of the gate/source voltage $V_{GS}$.

For the coating with indium zinc oxide, two solutions having a content of 1% by weight of the indium and zinc complexes with nitrodimethyl malonate described above in methoxyethanol are prepared. 1 g (In) and 0.24 g (Zn) thereof are subsequently mixed, so that the IZO precursor solution has an In:Zn molar ratio of 70:30. The IZO precursor solution is applied to the substrates described above by spin coating (1000 rpm for 10 s followed by 2000 rpm for 20 s) and calcined at 350° C. on a hotplate for 4 minutes. The coating is subsequently repeated for application of a second layer.

For the coating with zinc oxide, a solution having a content of 1% by weight of the zinc complex with nitromalonamide described above in methoxy-ethanol is prepared. The precursor solution is applied to the substrates described above by spin coating (1000 rpm for 10 s followed by 2000 rpm for 20 s) and calcined at 350° C. on a hotplate for 4 minutes. The coating is subsequently repeated for application of two further layers.

Example 9

Production of a Capacitor

Substrates for the production of capacitors usually consist of glass (1.5×1.5 cm²), to which rectangular areas of indium tin oxide are applied by sputter coating and an etching process. (The areas have different sizes. Two areas measuring 2 mm×0.99 mm, two areas measuring 2 mm×0.975 mm and two areas measuring 2 mm×0.95 mm are located on a substrate. For better contacting, gold (40 nm) having an area of 0.8 mm×1 mm is furthermore deposited overlapping part of the ITO areas by means of sputter coating via a mask. For the coating with zirconium dioxide, a solution having a content of 10% by weight of the zirconium complex with nitrodimethyl malonate described above in methoxyethanol is prepared. This is applied to the substrate by means of spin coating (1500 rpm for 30 s) and calcined at 350° C. on a hotplate for 20 s. The process is repeated, so that in total three layers are applied. The substrate is then finally processed with all three layers for a further 5 minutes at 350° C. on the hotplate. Gold electrodes (40 nm) (three different areas measuring 230×990 µm, 230×975 µm and 230×950 µm) are subsequently deposited transversely over the positions of the ITO areas by means of sputter coating via a mask. For the measurement, the contacting is carried out on the bottom or top of the layer of zirconium dioxide via the above-mentioned gold contacts on the ITO and the gold electrodes subsequently applied. The alternating-current resistance can thus be measured as a complex-valued function of the frequency, from which the capacitance of the capacitor and consequently the permittivity of the insulator for a known layer thickness can be determined.

By measurement of the electrical parameters, it has been found that the metal-oxide layers produced in accordance with the invention advantageously differ from known products in their physical properties. For illustration, the measured data are depicted graphically below. The graphical representations reproduced in the annex show the following:

The intensity is shown against the diffraction angle [2θ].

Figure 1:
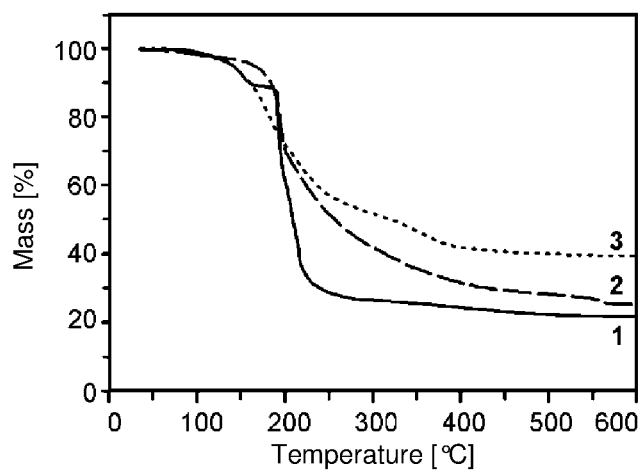
FIG. 1: Thermal decomposition of the zinc complexes with nitromalonamide (1), hydroxyiminodimethyl malonate (2) and nitrodimethyl malonate (3). The decomposition [% by weight] is shown as a function of the temperature [° C].
Figure 2:
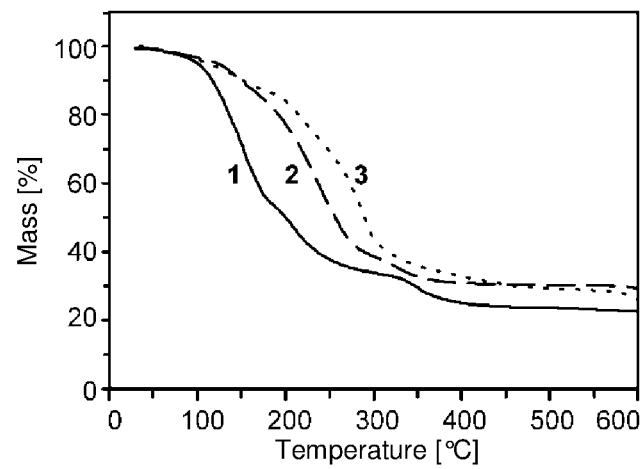
FIG. 2: Thermal decomposition of the zirconium complexes with nitrodimethyl malonate (1), methylsulfonyldimethyl malonate (2) and hydroxyiminodimethyl malonate (3). The decomposition [% by weight] is shown as a function of the temperature [° C].
Figure 3:
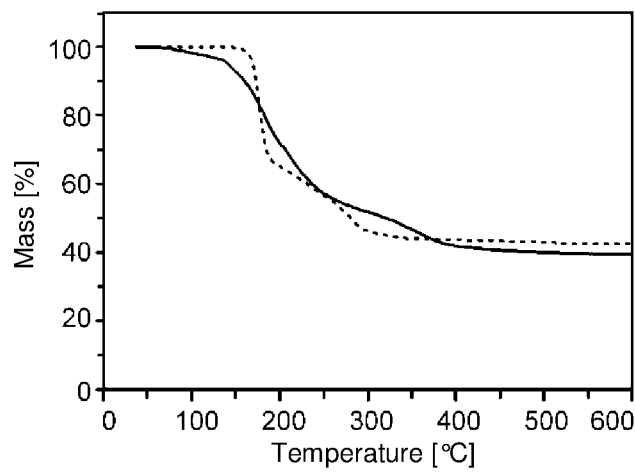
FIG. 3: Thermal decomposition of the zinc complexes (continuous curve) and indium complexes (dashed curve) with nitrodimethyl malonate. The decomposition [% by weight] is shown as a function of the temperature [° C].
Figure 4:
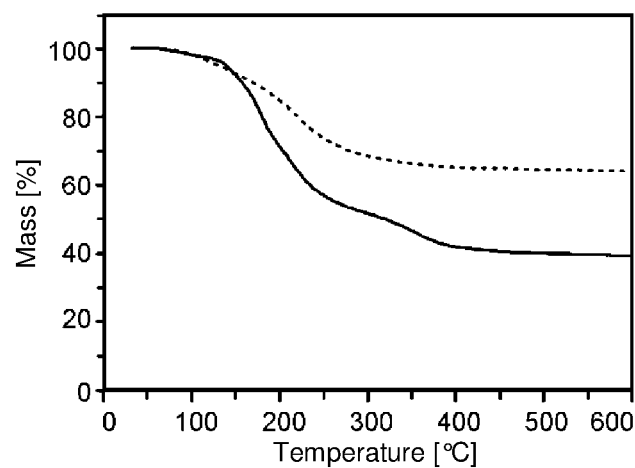
FIG. 4: Thermal decomposition of the zinc complexes (continuous curve) and tin(II) complexes (dashed curve) with nitrodimethyl malonate. The decomposition [% by weight] is shown as a function of the temperature [° C].
Figure 5:
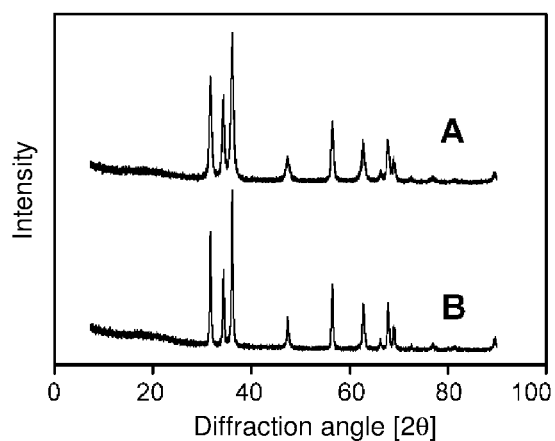
FIG. 5: X-ray diffraction pattern of powders comprising the zinc complex of nitrodimethyl malonate after calcination at temperatures of (A) 450° C. and (B) 600° C. The reflections observed show the formation of crystalline zincite.
Figure 6:
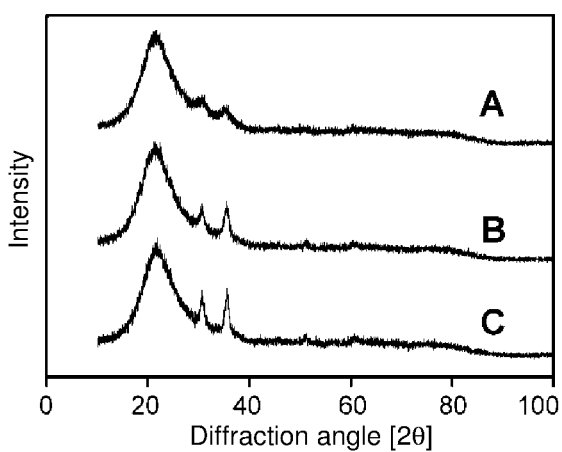

FIG. 6: X-ray diffraction pattern of powders comprising the indium complex of nitrodimethyl malonate after calcination at temperatures of (A) 250° C. and (B) 350° C. The reflections observed show the formation of nanocrystalline bixbyite.

The intensity is shown against the diffraction angle [2θ].

Figure 7:
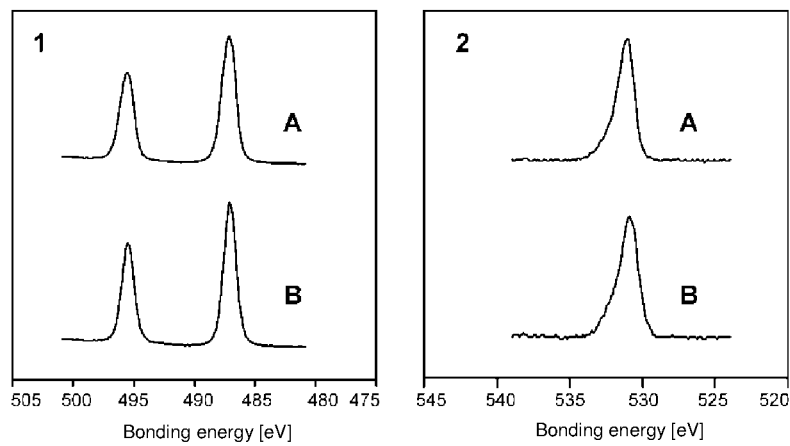

FIG. 7: X-ray photoelectron spectra in the region of the (1) Sn 3d and (2) O 1s signals of ceramic films comprising the tin(II) complex of nitro-dimethyl malonate after calcination at (A) 270° C. and (B) 460° C. The spectra show that exclusively tin(IV) oxide has been formed. It is present in the case of elemental tin or tin(II) oxide.

The bonding energy [eV] is shown.

Figure 8:
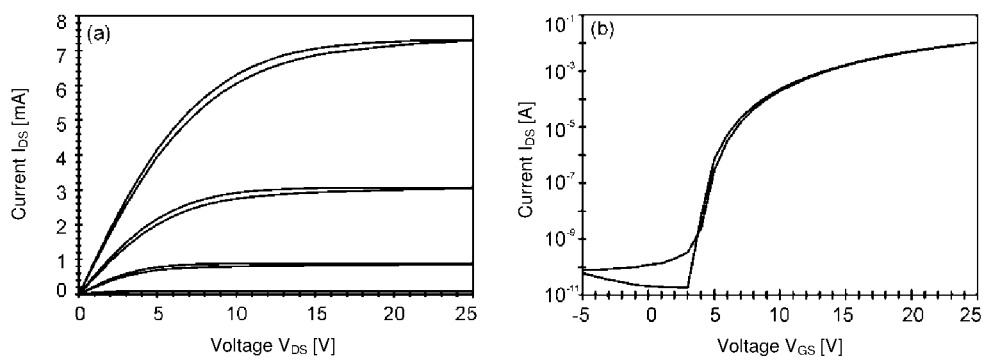

FIG. 8: Transistor characteristic lines of a film comprising indium zinc oxide after calcination at 350° C. in air. (a) Output characteristics for increasing and decreasing drain/source voltages at constant gate/source voltages of 0-25 V in 5 V steps. (b) Transfer characteristics at constant drain/source voltage of 25 V. The following characteristic quantities were obtained from the curve fitting: µ2.8 cm²/(Vs), $V_{th}$ 9.8 V and $I_{on/off}$~2*10⁸.

The measured current $I_{DS}$ [mA] is shown against the voltage $V_{DS}$ [V] and voltage $V_{GS}$ [V].

Figure 9:
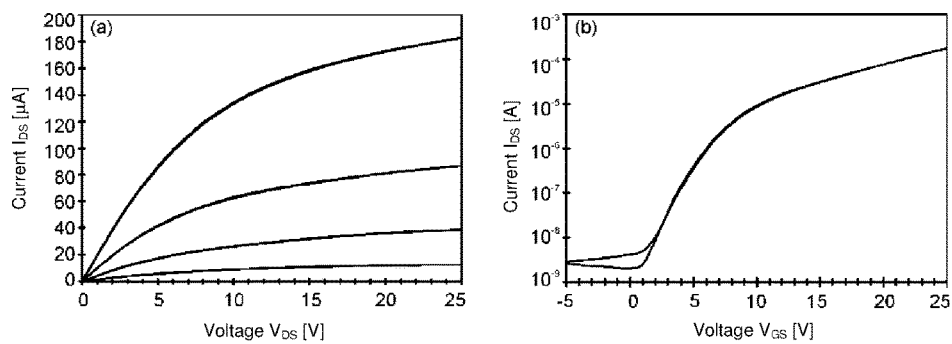

FIG. 9: Transistor characteristic lines of a film comprising zinc oxide after calcination at 350° C. in air. (a) Output characteristics for increasing and decreasing drain/source voltages at constant gate/source voltages of 0-25 V in 5 V steps. (b) Transfer characteristics at constant drain/source voltage of 25 V. The following characteristic quantities were obtained from the curve fitting: µ0.03 cm²/(Vs); $V_{th}$+6.3 V and $I_{on/off}$~3*10⁵. The measured current $I_{DS}$ [mA] is shown against the voltage $V_{DS}$ [V] and voltage $V_{GS}$ [V].

Figure 10:
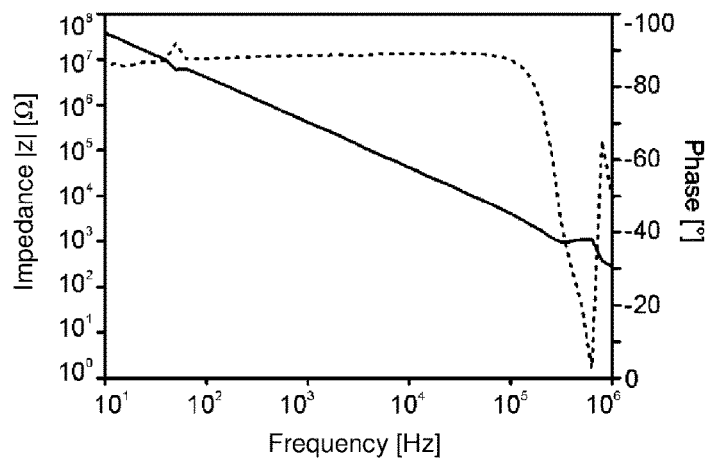

FIG. 10: Impedance and phase as a function of the alternating-current frequency measured on an insulator layer comprising zirconium dioxide. The determined impedance IzI [Ω] is shown against the frequency [Hz].

The invention claimed is:

1. A process for preparing a thin metal-oxide layer, dissolving or dispersing one or more metal complex(es) according to formula (I) or a metal-complex cluster thereof in a solvent or solvent mixture $$M_l[R^1—CO—C(H)_mX—CO—R^2]_n,\qquad(I)$$

in which
M denotes a metal atom selected from zinc, indium, gallium, tin, aluminum, zirconium, titanium and hafnium,
l denotes 1 or 2,
m denotes 0 or 1,
n denotes 1, 2, 3 or 4,
$R^1$ and $R^2$, independently of one another, denote alkyl having 1 to 8 C atoms, cycloalkyl having 3 to 7 C atoms, alkoxy having 1 to 8 C atoms and/or amino, $NHR^3$ or $NR^3R^4$, where $R^3$ and $R^4$, independently of one another, denote alkyl having 1 to 8 C atoms or cycloalkyl having 3 to 7 C atoms,
and
X denotes hydroxyimino, nitro, sulfo, —SO₂-alkyl having 1 to 8 C atoms, phosphato, —PO(O—R*)₂ where R* is alkyl having 1 to 8 C atoms or alkoxy having 1 to 8 C atoms, —SnR₃ where R is alkyl having 1 to 8 C atoms; —SR* where R* is H, alkyl having 1 to 8 C atoms or cycloalkyl having 3 to 7 C atoms, halide, or pseudohalide;
optionally adding to the solution or dispersion obtained liquefiers, stabilizers, binders and/or antifoams, applying the solution or dispersion obtained by wet coating to a substrate surface to be coated to form a layer, drying the applied layer and converting the applied layer into a metal oxide in the form of a thin layer by heating and calcination at a temperature in the range of 150-350° C.

2. The process according to claim 1, wherein said solution or dispersion comprises a solvent selected from methoxyethanol, dimethylformamide and dimethoxyethane, in pure form or in a mixture, optionally in the presence of water.

3. The process according to claim 1, wherein said solution or dispersion is applied to the substrate surface by spin coating, dip coating, spray coating, ink-jet printing, flexographic printing or gravure printing.

4. The process according to claim 1, wherein thin oxide layers of the metals zinc, indium, gallium, tin, aluminum, zirconium, titanium and/or hafnium are produced in which oxides are present in pure form or in a mixture, or as mixed oxides.

5. The process according to claim 1, wherein said solution or dispersion is applied a plurality of times to the substrate surface before the heating and calcination, with each layer is dried and heated individually.

6. A process according to claim 1, wherein the conversion of the applied layer into a metal oxide in the form of a thin layer is performed in by UV or IR irradiation.

7. A process according to claim 1, wherein the conversion of the applied layer into a metal oxide in the form of a thin layer is performed in by laser irradiation.

8. A process according to claim 1, wherein X is $-SO_2$-alkyl having 1 to 8 C atoms, $-PO(O-R^*)_2$ where $R^*$ is alkyl having 1 to 8 C atoms or alkoxy having 1 to 8 C atoms, $-SnR^{}_3$ where $R^{}$ is alkyl having 1 to 8 C atoms, $-SR^{*}$ where $R^{*}$ is H, alkyl having 1 to 8 C atoms or cycloalkyl having 3 to 7 C atoms, F, Cl, Br, I, $-CN$, $-N_3$, $-OCN$, $-NCO$, $-CNO$, $-SCN$ or $-SeCN$.

9. The process according to claim 1, wherein conversion of the applied, dried metal-complex layer is carried out by heating and calcination at temperatures in the range from 250-350° C.

10. A process according to claim 1, wherein the conversion of the applied layer into a metal oxide in the form of a thin layer is performed in by heating in an oven or on a hotplate.

11. The process according to claim 1, wherein the metal complex of formula (I) is a zinc complex with nitrodimethyl malonate, a zinc complex with hydroxyiminodimethyl malonate, a zinc complex with nitromalonic acid diamide, a tin(II) complex with nitrodimethyl malonate, an indium complex with nitrodimethyl malonate, a zirconium complex with hydroxyiminodimethyl malonate, or a zirconium complex with nitrodimethyl malonate.

* * * * *